United States Patent [19]

Kitamura et al.

[11] 4,242,302

[45] Dec. 30, 1980

[54] METHOD OF MAKING A CATALYTIC COMBUSTION TYPE GAS DETECTOR

[75] Inventors: Kenzo Kitamura, Tokyo; Hideaki Ebitani, Omiya; Masahiro Asakura, Urawa, all of Japan

[73] Assignee: Kabushiki Kaisha Shibaura Denshi Seisakusho, Urawa, Japan

[21] Appl. No.: 936,032

[22] Filed: Aug. 23, 1978

[30] Foreign Application Priority Data

Sep. 2, 1977 [JP] Japan .................................. 52/105434

[51] Int. Cl.³ ............................................. G01N 27/16
[52] U.S. Cl. ................. 422/94; 324/71 SN; 338/34; 23/232 E; 422/98; 422/88
[58] Field of Search .......... 422/98, 94, 95, 96, 422/97; 324/71 SN, 65 P; 338/34, 35; 23/232 E

[56] References Cited

U.S. PATENT DOCUMENTS

| 4,015,230 | 3/1977 | Nitta et al. | 338/35 |
| 4,086,556 | 4/1978 | Nitta et al. | 338/34 |

FOREIGN PATENT DOCUMENTS

| 2603785 | 8/1977 | Fed. Rep. of Germany | 324/71 SN |
| 51-33696 | 3/1976 | Japan | 324/71 SN |

Primary Examiner—R. E. Serwin

[57] ABSTRACT

A method is described of making a catalytic combustion type gas detector, the sensitivity of which to alcohol vapors and to tobacco fumes is decreased by utilizing a mixture of powders. The mixed powders is composed of at least one metal oxide selected from $TiO_2$, $ZrO_2$, $Y_2O_3$, $HfO_2$, $CeO_2$, $La_2O_3$, NiO $Cr_2O_3$ and a substance which presents an N-type semiconductor characteristic by gas adsorption. The mixture is coated directly on a wire coil of Pt or the like and a current is applied to the metal wire coil in an oxidizing atmosphere to sinter the coated mixed powder thereon.

6 Claims, 3 Drawing Figures

METHOD OF MAKING A CATALYTIC COMBUSTION TYPE GAS DETECTOR

BACKGROUND OF THE INVENTION

1. Field of the Invention

This invention relates to a method of making a catalytic combustion type gas detector which utilizes the catalytic action of a sintered, high-melting metal oxide such as $TiO_2$, $ZrO_2$, $HfO_2$, $Y_2O_3$, $CeO_2$, $NiO$, $Cr_2O_3$ or equivalent and which has selectively decreased sensitivity to alcohol vapors and to tobacco fumes.

2. Description of the Prior Art

Catalytic combustion type gas detectors heretofore employed were generally utilizing as catalyst a metal of the platinum group and fixed on a carrier such as alumina or the like. These conventional gas detectors have the defects of being highly susceptible to catalytic poisoning and to moisture, resulting in a marked degradation of the catalytic action, in a high concentration of flammable gas and in high manufacturing costs. The present inventors discovered that the abovesaid defects could be overcome by exploiting the catalytic action of a sintered, high-melting metal oxide such as $TiO_2$, $ZrO_2$, $Cr_2O_3$, $NiO$, $CeO_2$, $HfO_2$, $Y_2O_3$ or equivalent, as fully described in Japanese Pat. Appln. No. 17877/77 filed on Sept. 2, 1977. According to said Japanese patent application, a catalytic combustion type gas detector based on this technical idea may be made by choosing the special metal oxides as a catalyst. However, it has been found that this gas detector, utilizing the catalytic action of the abovesaid sintered metal oxide, although exhibiting high resistance to catalytic poison and very little degradation in catalytic activity in a high concentration of flammable gas, is unfortunately too sensitive to alcohol vapors and to tobacco fumes, more so than to other gases and vapors. For example, in the case of a gas detector using a sintered ternary metal oxide of $TiO_2$—$ZrO_2$—$Cr_2O_3$, letting the sensitivity to i-$C_4H_{10}$ at a concentration of 2,000 ppm be represented by 1, the sensitivity to $C_2H_5OH$ at the same concentration is about 2.9. Accordingly, when employed as LPG (liquified petroleum gas) sensor for home use, such a gas detector would raise an erroneous alarm in answer to alcohol vapors given off by, for example, cooking with wines or spirits and hence is not fully reliable as a gas sensor. As will be described later on, the sensitivity ratio of tobacco fumes to i-$C_4H_{10}$ vapors is about 1.2, that is, the abovesaid gas detector has a higher sensitivity to the former, so that it is likely to given an erroneous warning, for example, when tobacco fumes exist at sufficiently high concentrations.

SUMMARY OF THE INVENTION

An object of this invention is to provide a method of making a highly reliable and inexpensive catalytic combustion type gas detector which retains the excellent features obtained by utilizing the catalytic action of a sintered, high-melting metal oxide, such as $TiO_2$, $ZrO_2$, $HfO_2$, $Y_2O_3$, $CeO_2$, $NiO$, $Cr_2O_3$ or equivalent, and concurrently possesses sensitivities to alcohol vapors and to tobacco fumes that are selectively decreased to useful levels.

Another object of this invention is to provide a method of making a gas detector in which the above features can be achieved by adding to the abovementioned high-melting metal oxide a predetermined amount of a substance which exhibits an N-type semiconductor characteristic by gas adsorption.

Briefly stated, in the present invention, a mixed powder of (a) at least one metal oxide selected from the group consisting of $TiO_2$, $ZrO_2$, $Y_2O_3$, $HfO_2$, $CeO_2$, $La_2O_3$, $NiO$ and $Cr_2O_3$ and (b) less than 40 weight % (based on the weight of the mixture) of a substance which exhibits an N-type semiconductor characteristic by gas adsorption is coated and fixed directly on a metal wire (suitably a wire coil) which is hard to oxidize at high temperatures. Then, a current is applied to the coated metal wire to sinter the mixture powder at temperatures higher than 1,000° C. but lower than the melting point of the wire.

DESCRIPTION OF THE PREFERRED EMBODIMENTS

A metal wire (suitably a wire coil) for use in this invention is required not to be oxidized at high temperatures, and hence is restricted to metals of the platinum group, such as platinum, platinoiridium, platinopalladium, platinorhodium or equivalent, with a melting point of the order of about 1,700° C. In particular, a platinum coil is preferred in view of its resistance-temperature coefficient. The diameter of the metal wire is not specified but is approximately 0.05 mm.

Figure 1:
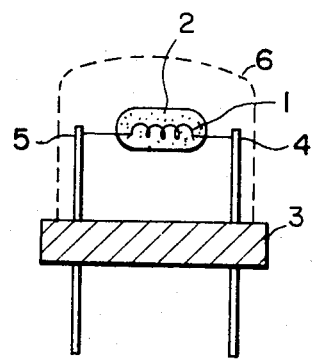
FIG. 1 is a schematic illustration of an embodiment of a gas detector produced according to this invention.

In accordance with this invention, a powder of at least one metal oxide selected from the group consisting of $TiO_2$, $ZrO_2$, $HfO_2$, $Y_2O_3$, $CeO_2$, $NiO$ and $Cr_2O_3$, is mixed with less than 40% by weight (based on the mixture) of a substance, the electrical resistance of which is decreased by gas adsorption to provide an N-type semiconductor characteristic. The resulting mixed powder, identified at 2 in FIG. 1, is kneaded with pure water and coated directly on metal wire coil 1, which is not easily oxidized at high temperatures, and is dried and fixed to coil 1 to provide a bead-like element, as shown in FIG. 1. After this element is mounted, as by electric welding, on terminals 4 and 5 of a stem-base 3, a current is applied across the said terminals in the open air, whereby the coated mixture powder 2 is firmly sintered, the mean temperature of the metal wire coil 1 in terms of its resistance-temperature coefficient being held at above 1,000° C. but below the melting point of the coil. Then, a net-like cap 6 is put on the element and is sealed to complete the gas detector.

Substances which exhibit the N-type semiconductor characteristic by gas adsorption, include among others $ZnO$, $SnO_2$, $In_2O_3$. The abovesaid sintering temperature condition is necessary not only for retaining the mechanical strength of the sintered member but also for sintering the mixed powder at a temperature high enough to neglect a temperature rise in the case of a flammable gas burning on the surface of the sintered member so as to prevent an abrupt change in the property of the catalyst in the burning of the flammable gas. Although it is most preferable to raise the sintering temperature of the metal oxides to the vicinity of the melting point of the metal wire coil, the sintering should be performed at the temperature where the above said metal oxide is not decomposed and the sintering does not proceed rapidly. And in the case where the metal oxide melts at a temperature below the melting point of the metal wire coil or sintering rapidly proceeds, the catalytic action is lost, so that the melting point of the metal oxide must be higher than that of the metal wire coil. Further, the lower limit of the sintering temperature is required to be higher than 1,000° C. for maintaining the mechanical strength of the sintered metal oxide which ultimately serves as a catalyst. The abovesaid mean temperature of 1,000° C. for the metal wire coil is a value in terms of the resistance-temperature coefficient of the coil, the temperature at the central portion of the metal wire coil being actually higher than the abovementioned mean temperature; namely about 1.2 to 1.5 times the mean temperature, though differing with the length of the coil and the amount of sintered metal oxide used. The particle size of the metal oxide powder is selected to range from 1 to 50 microns and the powder must be coated on the metal wire coil in an amount sufficient to be packed around the coil and to completely cover it; otherwise the mechanical strength of the abovesaid sintered member is reduced.

The present invention requires electric heating for the sintering operation, because the activity of a catalyst usually takes the form of chemical adsorption of unsaturated atoms, and the activity points of the catalyst have charged potential. When such a substance is heated in an ordinary heating furnace to sintering temperature, there occurs a migration of atoms and a change in the wave number vector such that the energy level and the density of the abovesaid potential are minimized, and if the heated member is cooled as it is, the activity points of the catalyst decrease. In this invention, since heating is performed by energizing the metal wire coil coated with the metal oxide catalyst, the catalyst is always applied an electrical field and heated, with the potential retaining the energy level and density of the electrical field, and even if the catalyst is cooled, the potential is not greatly lost. In other words, heating by such energization technique provides a metal oxide sintered member which does not lose its function when heated at sintering temperatures. In the present invention, a supply of oxygen is indispensable to the sintering; it is necessary that at least 10% oxygen be present in an inert gas stream. When the amount of oxygen is less than 10%, oxygen in the metal oxide dissociates to lower the catalytic function. Useful inert gases include argon, nitrogen and the like.

The main feature of this invention is that the abovesaid metal oxide contains a substance which presents an N-type semiconductor characteristic by gas adsorption, such as, for example, $ZnO$, $SnO_2$ or $In_2O_3$. These substances have a stronger action for adsorbing $C_2H_5OH$ vapors and tobacco fumes rather than i-$C_4H_{10}$ vapors, and have the property that the electrical resistance is decreased by the gas adsorption. The amount of such substance added is less than 40% by weight, preferably 10 to 35% by weight, based on the weight of the powder mixture.

As described above, in the gas detector of this invention, since the N-type semiconductor, i.e. $ZnO$, $SnO_2$, $In_2O_3$ or the like, is contained in the high-melting metal oxide sintered member coated onto the surface of the metal wire coil, when the gas detector is exposed to alcohol vapors or to tobacco fumes, the abovesaid $ZnO$, $SnO_2$, $In_2O_3$ or the like rapidly absorbs the said vapors or fumes and reduces its electrical resistance; thus the sensitivity to alcohol vapors and to tobacco fumes is selectively lowered. Accordingly, when employed as an LPG sensor for home use, the gas detector of this invention does not ever give an erroneous signal in the presence of alcohol vapors or tobacco fumes. Furthermore, the gas detector of this invention retains all of the other excellent features such as high resistance to catalytic poisoning, little degradation of the catalytic function in a humid atmosphere or in a high concentration of flammable gas, features obtained by making use of the catalytic action of the high-melting metal oxide sintered member per se.

The present invention will be further described in connection with some specific operative examples, which are to be construed as merely illustrative of the invention and not limitative thereof.

EXAMPLES 1-16

In each of Examples 1-16, and following the construction of FIG. 1, a powder of at least one high-melting metal oxide selected from the group consisting of $TiO_2$, $ZrO_2$, $Y_2O_3$, $HfO_2$, $CeO_2$, $La_2O_3$, $NiO$ and $Cr_2O_3$ and a powder of an N-type semiconductor, $ZnO$, $SnO_2$ or $In_2O_3$, with electrical resistance reduced by gas adsorption, were mixed together in the weight ratio shown in Table 1. The mixture was kneaded with pure water and coated on a platinum wire coil having a diameter of 0.05 mm, dried and fixed to the coil to provide an element. This element was attached by electric welding atop the two terminals of a stem base, and then a current was applied across the terminals to firmly sinter the coated mixed powder in the open air, with the mean temperature of the platinum wire coil held at 1,250° C. Then, a net-like cap was put on the sintered member and sealed to obtain a gas detector as shown in FIG. 1.

Figure 2:
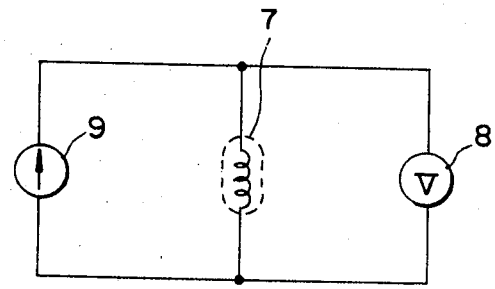
FIG. 2 shows a sensitivity measuring circuit for i-$C_4H_{10}$, $C_2H_5OH$ and tobacco fumes in the gas detector of FIG. 1.

The sensitivities of the sixteen gas detectors to i-$C_4H_{10}$ and $C_2H_5OH$ vapors and tobacco fumes were each measured as a change in the terminal voltage by a circuit like that shown in FIG. 2. The measured results are given in Table 2. In FIG. 2, reference numeral 7 indicates the gas detector; 8 designates a voltmeter; and 9 identifies a source of constant-current. 250 mA were applied to maintain the element at about 400° C. The concentrations of the i-$C_4H_{10}$ and $C_2H_5OH$ vapors were each 2,000 ppm, and the tobacco fumes were obtained by spontaneous combustion of one cigarette.

For comparison purposes, there are also shown in Tables 1 and 2 two comparative examples (1 and 2) with the composition ratio of high-melting metal oxides employed in a conventional gas detector, but excluding any of the abovesaid substances ($ZnO$, $SnO_2$ or $In_2O_3$).

As it is evident from Tables 1 and 2, the gas detector of each of Examples 1-16 has markedly lower sensitivity to $C_2H_5OH$ vapors and to tobacco fumes without nevertheless decreasing its sensitivity to i-$C_4H_{10}$ vapors, as compared with the gas detectors of the comparative examples 1 and 2. The reason is that $ZnO$, $SnO_2$ and $In_2O_3$, which become N-type semiconductors by gas adsorption, are stronger adsorbers for the $C_2H_5OH$ vapors and the tobacco fumes than for the i-$C_4H_{10}$ vapors, and their electrical resistance is reduced by the adsorption of such gases.

Figure 3:
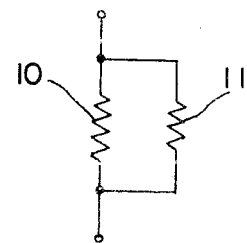
FIG. 3 is an illustrative explanation of the operational principle of the gas detector of FIG. 1.

Referring now to FIG. 3, the operational principle of the gas detector of Example 7 will be described, by way of example.

In FIG. 3, reference numeral 10 and 11 indicate resistances of the platinum wire coil and the N-type semiconductor, respectively. Usually a current of about 250 mA is applied across both resistances to heat the coil to about 400° C. and, in such a case, resistances 10 and 11 are about 5 and 4 Kilo-ohms respectively. In such a state, when the gas detector contacts the i-$C_4H_{10}$ vapor, combustion starts due to the catalytic action of the sintered $Cr_2O_3$-NiO, and resistance 10 tends to increase by about 0.2 ohms up to 5.2 ohms when the i-$C_4H_{10}$ vapor concentration is 2,000 ppm, but resistance 11 of the N-type semiconductor decreases to about 2 Kilo-ohms to provide a composite resistance of 5.187 ohms. As a result, the terminal voltage undergoes a change of 47 mV; namely, the influence of the N-type semiconductor is not great. The reason is that the N-type semiconductor, ZnO, is relatively weak in adsorbing the i-$C_4H_{10}$ vapor.

On the other hand, in the case of the $C_2H_5OH$ vapor, resistance 10 tends to increase by about 0.3 ohms up to 5.3 ohms, but resistance 11 decreases to approximately 200 ohms to provide a composite resistance of 5.163 ohms with the result that the terminal voltage changes by 41 mV. The reason for such a decrease in the terminal voltage fluctuation is that, although resistance 10 is increased, resistance 11 is much greatly decreased by the strong action of adsorption of the $C_2H_5OH$ vapor on the part of the N-type semiconductor.

On such principle, only the sensitivity to $C_2H_5OH$ vapors and to tobacco fumes can be sharply reduced without seriously impairing the sensitivity to the i-$C_4OH_{10}$ vapor. But, as it can be seen from Examples 8 through 10 in Table 2, when the amount of N-type semiconductor added is 40% by weight, the i-$C_4H_{10}$ vapor adsorbing ability of the N-type semiconductor increases abruptly, and the sensitivity to the i-$C_4H_{10}$ vapor becomes lower than the sensitivity to the $C_2H_5OH$ vapor. Accordingly, the amount of N-type semiconductor to be added should be less than 40% by weight, preferably in the range of from 10 to 35% by weight, based on the total weight of the powder mixture. With less than 10% by weight of N-type semiconductor added, the adsorbing ability for $C_2H_5OH$ vapor and tobacco fumes is lowered.

A normal alarm concentration of an LPG sensor for home use is officially determined to be 0.1 to 0.3% in terms of i-$C_4H_{10}$ vapor, and it is pre-set in general, to give the alarm at a concentration of 0.2%. In the case of applying this to the sample of Example 1, when the alarm concentration is 2,000 ppm in terms of the i-$C_4H_{10}$ vapor, the concentration at which to give a warning against the $C_2H_5OH$ vapor is (55 mV/40 mV)×2,000 ppm=2,750 ppm, sufficiently fulfilling the general restriction that no alarm be raised at a $C_2H_5OH$ concentration of 1,000 ppm. Speaking of tobacco fumes, no warning is given unless (55 mV/25 mV)×1 cigarette=2.2 cigarettes are burnt.

Further, in the case of the sample of comparative example 2, the alarm concentration of the $C_2H_5OH$ vapor is (36 mV/80 mV)×2,000 ppm=900 ppm, and a false alarm is raised at a $C_2H_5OH$ vapor concentration of only 1,000 ppm. In the case of tobacco fumes, a warning is given when (36 mV/43 mV)×1=0.83 cigarette is burnt.

Accordingly, in order that an alarm may not be given at a $C_2H_5OH$ vapor concentration of 1,000 ppm, even in the worst case of an alarm concentration of the i-$C_4H_{10}$ vapor of 1,000 ppm, it suffices that the sensitivity to i-$C_4H_{10}$ vapor be higher than the sensitivity to $C_2H_5OH$ vapor.

It will be apparent that many modifications and variations may be effected without departing from the scope of the novel concepts of this invention.

TABLE 1

| Example No. | $Cr_2O_3$ | $TiO_2$ | $ZrO_2$ | $Y_2O_3$ | $HfO_2$ | $CeO_2$ | $La_2O_3$ | NiO | ZnO | $SnO_2$ | $In_2O_3$ |
|---|---|---|---|---|---|---|---|---|---|---|---|
| 1 | 90 | | | | | | | | 10 | | |
| 2 | 65 | | | | | | | | 35 | | |
| 3 | 60 | | | | | | | | 40 | | |
| 4 | 50 | 30 | | | | | | | 20 | | |
| 5 | 50 | | 30 | | | | | | 20 | | |
| 6 | 50 | | | 30 | | | | | 20 | | |
| 7 | 70 | | | | | | | 20 | 10 | | |
| 8 | 90 | | | | | | | | | 10 | |
| 9 | 65 | | | | | | | | | 35 | |
| 10 | 60 | | | | | | | | | 40 | |
| 11 | 50 | | | | 40 | | | | | 10 | |
| 12 | 50 | | | | | 40 | | | | 10 | |
| 13 | 50 | | | | | | 40 | | | 10 | |
| 14 | 90 | | | | | | | | | | 10 |
| 15 | 65 | | | | | | | | | | 35 |
| 16 | 60 | | | | | | | | | | 40 |
| C1 | 90 | | | 10 | | | | | | | |
| C2 | 50 | 25 | 25 | | | | | | | | |

Notes:
The compositions are on a weight % basis C1 and C2 are comparative examples

TABLE 2

| | (millivolts of:) | | |
|---|---|---|---|
| No. | i-$C_4H_{10}$ | $C_2H_5OH$ | Tobacco fumes |
| 1 | 55 | 40 | 25 |
| 2 | 30 | 40 | 18 |
| 3 | 25 | 39 | 19 |
| 4 | 45 | 45 | 29 |
| 5 | 53 | 48 | 34 |
| 6 | 49 | 45 | 31 |
| 7 | 47 | 41 | 30 |
| 8 | 43 | 44 | 38 |
| 9 | 27 | 38 | 29 |
| 10 | 22 | 33 | 25 |
| 11 | 38 | 31 | 29 |
| 12 | 33 | 30 | 27 |
| 13 | 39 | 31 | 24 |
| 14 | 40 | 39 | 36 |
| 15 | 21 | 24 | 22 |
| 16 | 16 | 21 | 20 |
| C1 | 41 | 85 | 40 |
| C2 | 36 | 80 | 43 |

What is claimed is:
1. A method of making a gas detector comprising the steps of:

mixing at least one powdered metal oxide selected from the group consisting of $TiO_2$, $ZrO_2$, $Y_2O_3$, $HfO_2$, $CeO_2$, $La_2O_3$, NiO and $Cr_2O_3$ with a powdered substance which exhibits an N-type semiconductor characteristic by gas adsorption and which is selected from the group consisting of ZnO, SnO and $In_2O_3$, said powdered substance being in an amount of less than 40% by weight, based on the total weight of the powders;

coating the thus mixed powders on a wire coil of a metal which is difficult to become oxidized at elevated temperatures; and applying an electric current to said metal wire coil in an oxidizing atmosphere to sinter the thus coated wire coil, the mean temperature of said wire coil during sintering being greater than 1000° C. but lower than the melting point of the said metal wire coil.

2. The method according to claim 1, which is for making a detector which is selective for alcohol fumes and tobacco fumes.

3. The method according to claim 1 wherein said amount of said powdered substance ranges between 10 and 35% by weight, based on the total weight of the powders.

4. A gas detector which comprises:
(a) a wire coil of a metal which is difficult to become oxidized at elevated temperatures;
(b) a pair of electric terminal conductors connected to said wire coil;
(c) a mixture of a first powder and a second powder coated and sintered onto said wire coil; said first powder consisting of an oxide selected from the group consisting of $TiO_2$, $ZrO_2$, $Y_2O_3$, $HfO_2$, $CeO_2$, $La_2O_3$, NiO and $Cr_2O_3$, and said second powder consisting of an oxide selected from the group consisting of ZnO, $SnO_2$ and $In_2O_3$; said second powder being in an amount of less than 40% by weight, based on the total weight of the mixture;
(d) a stem-base for supporting rigidly thereon said terminal conductors; and
(e) an encapsulating envelope enclosing said coated wire coil into an operating unit.

5. The gas detector according to claim 4, for detecting selectively fumes of alcohol and tobacco.

6. The gas detector according to claim 4, wherein said second powder is in an amount of between 10 and 35% by weight, based on the total weight of the mixture.

* * * * *